United States Patent [19]
Kojima et al.

[11] Patent Number: 5,945,298
[45] Date of Patent: *Aug. 31, 1999

[54] METHOD FOR ASSAYING BILIRUBIN δ FRACTIONS

[75] Inventors: Ryo Kojima; Yoshikiyo Sasagawa; Katsuhiro Katayama, all of Koriyama, Japan

[73] Assignee: Nitto Boseki Co., Ltd., Fukushima, Japan

[ * ] Notice: This patent is subject to a terminal disclaimer.

[21] Appl. No.: 09/030,830

[22] Filed: Feb. 26, 1998

[30] Foreign Application Priority Data

Feb. 28, 1997 [JP] Japan ................................ 9-046133

[51] Int. Cl.$^6$ ....................................... C12Q 1/26
[52] U.S. Cl. ................................................ 435/25
[58] Field of Search ................................... 435/25

[56] References Cited

U.S. PATENT DOCUMENTS

| | | | |
|---|---|---|---|
| 4,211,844 | 7/1980 | Wu | 435/25 |
| 4,569,912 | 2/1986 | Matsui et al. | 435/25 |
| 4,600,689 | 7/1986 | Matsui et al. | 435/25 |
| 4,770,997 | 9/1988 | Yoshino et al. | 435/25 |
| 4,895,799 | 1/1990 | Kruse-Muller | 435/18 |
| 5,449,623 | 9/1995 | Tokuda et al. | 436/97 |

FOREIGN PATENT DOCUMENTS

| | | |
|---|---|---|
| 62-058999 | 3/1987 | Japan . |
| 62-105047 | 5/1987 | Japan . |
| 64-005499 | 1/1989 | Japan . |
| 5-18978 | 1/1993 | Japan . |
| 86/00933 | 2/1986 | WIPO . |
| 96-17251 | 6/1996 | WIPO . |

OTHER PUBLICATIONS

Yamamoto, Journal of the Japanese Society of International Medicine 78(11), pp. 36–41 (1989). (English Remarks).
Lauff et al., Clinical Chemistry, vol. 28, No. 4, pp. 629–637, (1982).
Lauff et al., Journal of Chromatography, 226, pp. 391–402, (1981).
Weiss et al., The New England Journal of Medicine, vol. 309, pp. 147–156, (1983).
Tan–Kan–Sul (Gallblader, Liver and Pancrease) 11(3), pp. 393–400 (1985). (English Remarks).
Nakumura et al., Bunsekikagaku, 36, pp. 352–355, (1987). (English Abstractand Remarks).
Adachi et al., Gastroenterologia Japonica, vol. 23, No. 3, pp. 268–272 (1988).
Kato, Medical Journal of Kinki University, vol. 14, No. 1, pp. 97–112, (1989) (English Abstract and Remarks).
Wu et al., Clin. Chem. vol. 30, No. 8, pp. 1304–1309, (1984).
Seibutsu Shiryo Bunseki (Biological Sample Analysis), 9(3), pp. 15–23 (1986) (English Remarks).
Umaji et al., Rinsho Byori (Clinical Pathology), vol. 37, No. 8, pp. 905–910, (1989) (English Abstract).
Lo et al., Clin. Chem. vol. 29, No. 1, pp. 31–36, (1983).
Doumas et al., Clin. Chem. vol. 19, No. 9, pp. 984–993, (1973).
Perry et al., Clin. Chem. vol. 32, No. 2, pp. 329–332, (1986).
Otsuji et al., Clinical Biochemistry, vol. 21, No. 1, pp. 33–38, (1988).

*Primary Examiner*—Jon P. Weber
*Attorney, Agent, or Firm*—Armostrong, Westerman, Hattori, McLeland & Naughaton

[57] ABSTRACT

By making a bilirubin oxidase derived from the genus Pleurotus to act on a living body fluid sample in the presence of at least one of a cationic surfactant such as alkyltrimethylammonium salt, etc. and a nonionic surfactant such as polyoxyethylenealkyl ether, etc., only bilirubin non-δ fractions of the living body fluid sample can be oxidized, while keeping a bilirubin δ fraction remaining as unreacted. Thus, the bilirubin non-δ fractions and δ fraction of the living body fluid sample can be exactly quantitatively determined by action of the bilirubin oxidase on the sample.

5 Claims, 4 Drawing Sheets

FRACTIONAL PATTERN OF SERUM BILIRUBIN BY HPLC

FRACTIONAL PATTERNS BEFORE AND
AFTER REACTION
(BILIRUBIN OXIDASE DERIVED FROM Pleurotus ostreatus)

CORRELATION BETWEEN CONCENTRATIONS OF NON-$\delta$ FRACTIONS BY HPLC AND THOSE BY THE PRESENT INVENTION CORRELATION BETWEEN CONCENTRATIONS OF δ FRACTION BY HPLC AND THOSE BY THE PRESENT INVENTION

METHOD FOR ASSAYING BILIRUBIN δ FRACTIONS

BACKGROUND OF THE INVENTION

1) Field of the Invention

The present invention relates to a method for assaying bilirubin fractions in living body fluid samples such as plasma, serum, urine, etc. and more particularly to a method for assaying bilirubin non-δ fractions and a bilirubin δ fraction in living body fluid samples, utilizing bilirubin oxidase incapable of oxidizing a bilirubin δ fraction but capable of oxidizing bilirubin non-δ fractions in the presence of at least one of a cationic surfactant and a nonionic surfactant, and also relates to an assay kit for use in the same method.

2) Description of the Related Art

Bilirubin is a metabolic product of hemoglobin originating from aged erythrocyte and constitutes the main component of bile pigment. Blood contains a fraction with increased water solubility (conjugate form) due to ester linkage of side chain propionate group of bilirubin mainly to glucuronic acid enzymatically in the liver and a fraction with decreased water solubility (free form) due to the propionate group remaining in a free state. The former is called "direct bilirubin" because of easy reaction with a diazo reagent, whereas the latter is determined as "indirect bilirubin" as subtracting the concentration of direct bilirubin from the concentration total bilirubin obtained by diazo dying of bilirubin in the presence of a reaction accelerator such as alcohol, etc., because reaction with the diazo reagent occurs only in the presence of the reaction accelerator.

By fractionally determining the concentrations of respective conjugate form and free form bilirubin, diacrisis and diagnosis of jaundice due to various liver diseases, hemolytic diseases, etc. can be made and thus assaying of bilirubin is an important item of examination in the clinical laboratory test.

Apart from the reactivity with a diazo reagent, fractional analysis of bilirubin by high performance liquid chromatography (HPLC) has been also studied. Bilirubin in serum is separated mainly into 4 fractions, i.e., α, β, γ and δ fractions by HPLC, where the α fraction is identified as free form bilirubin; the β fraction as bilirubin, one of whose two propionate groups in the molecule undergoes ester linkage to glucuronic acid (bilirubin monoglucuronide); the γ fraction as bilirubin, whose two propionate groups all undergo ester linkage to glucuronic acid (bilirubin diglucuronide); and the δ fraction as bilirubin in a covalent bond with albumin. Furthermore, it is presumed that the δ fraction results from non-enzymatic reaction of the γ fraction with albumin (Toshio Yamashita: Journal of The Japanese Society of Internal Medicine 78 (11), 36–41 (1989)).

According to the classification based on reactivity with a diazo reagent, it is presumed that the α fraction corresponds to indirect bilirubin and the β and γ fractions and also the δ fraction correspond to direct bilirubin (John J. Lauff: Clin. Chem. 28 (4), 629–637 (1982)).

The β and γ fractions are constituted from water-soluble low molecular weight compounds and thus can readily pass through renal glomeruli to be rapidly discharged into urine. That is, they never remain in blood for a long time. The δ fraction, on the other hand, can undergo metabolism not as bilirubin but rather as albumin, and it is presumed that the half life of the δ fraction in blood is as long as 2–3 weeks, whereas that of other fractions is as short as a few ten minutes (John J. Lauff: J. Chromatogr., 226, 391–402 (1981); J. S. Weis: N. Engl. J. Med., 309, 147–156 (1983)).

Assay results of serum bilirubin according to the conventional diazo method can supply important information on the initial phase of jaundice, particularly hyper-(direct form) bilirubinemia, but the diazo method has been so far considered to be uncapable of giving its assay results reflecting correctly and timely the progress changes in jaundice. This phenomenon is obviously due to the fact that reaction of the γ fraction with albumin can increase the δ fraction, apparently retarding the bilirubin metabolic rate, thereby causing a lag between the bilirubin assay results and the actual amelioration and/or deterioration of the disease. That is, it can be said that in case that there are a large amount of δ fraction having the slow metabolic process and also showing the reactivity with direct bilirubin in samples, the bilirubin assay results according to the diazo method have no more clinical significance, because the assay results involve also the high level δ bilirubin and will fail therefore to correctly reflect the progress of the disease. (Toshio Yamamoto: Tan-Kan-Sui (Gallblader, Liver and Pancrease), 11 (3), 393–400 (1985)).

In order to determine bilirubin concentrations sensitive to changing states of disease, attempts have been made for fractional quantitative determination of individual α to δ fractions, one of which is based on the above-mentioned HPLC method (John J. Lauff: J. Chromatogr., 226, 391–402 (1981)). Its improvements have been made by omitting complicated sample pretreatment steps as much as possible (Nakamura H.: Bunsekikagaku, 36, 352–355 (1987); Yukihiko Adachi: Gastroenterologia Japanica, 23 (3), 268–272 (1988); Yuko Kato: Medical Journal of Kinki University, 14 (1), 97–112 (1989)).

It was reported on the basis of these HPLC results that a ratio of individual bilirubin fractions such as δ/(β+γ+δ), (α+γ)/δ or β/δ sensitively reflects changing states of liver diseases and is particularly useful for prognostication. Assay of individual bilirubin fractions could solve the problems of bilirubin assay by the conventional diazo method, because information even on progress of state of disease could be obtained by only one assay, and thus has been regarded as having lifted the position of serum bilirubin in the liver function test (Toshio Yamamoto: Kan-Tan-Sui (Gallblader, Liver and Pancrease), 11 (3), 393–400 (1985)).

However, the HPLC method requires about one hour in the assay of one sample, even if the complicated pretreatments could be omitted, and thus can be regarded not as a practical method for assaying a large number of samples daily, but as a laboratory-scale research method.

On the other hand, Wu et al developed a dry chemistry method (Ektachem method) as a highly practical method for assaying bilirubin fractions on the basis of such a principle that proteins including the δ fraction can be separated and removed by a special membrane; then the low molecular weight bilirubin fraction having permeated through the membrane is made to react with cationic polymers; the free form bilirubin (α fraction) and the conjugate form bilirubin (β+γ fraction) can be fractionally and quantitatively determined at 400 nm and 460 nm, respectively, as a result of a change in the reflectance spectrum from each other, where the δ fraction can be obtained by subtracting the assay results of the free form bilirubin (α fraction) and the conjugate form bilirubin (β+γ fraction) from the assay result of total bilirubin obtained by the diazo method. That is, according to the Ektachem method, a total bilirubin concentration, a free form bilirubin (α fraction) concentration, a conjugate form bilirubin (β+γ fraction) concentration and a δ fraction concentration are fractionally and quantitatively determined, respectively (Tai-Wing Wu: Clin. Chem., 30 (8), 1304–1309 (1984)).

The Ektachem method can assay one sample in the order of a few minutes and thus can be regarded as a practically distinguished method for assaying fractions. It was reported that the assay results of the Ektachem method were in good agreement with those of the HPLC method in the hyper-(direct form)bilirubinemia, upon comparison thereof. However, it was also reported that in case that the total bilirubin concentration is in the normal range (not more than 1.3 mg/dl) or in case of hyper-(indirect form)bilirubinemia the assayed δ fraction of the Ektachem method considerably deviated from that of the HPLC method (Yukihiko Adachi: Gastroenterologia Japonica, 23 (3), 268–272 (1986)).

Furthermore, the Ektachem method has such a disadvantage as a strong influence of colored substances because of measurement of reflectance intensity (Young D. S.: Washington D.C. AACC Press (1990); Yound D. S.: 1991 Supplement. Washington D.C. AACC Press (1991); Friedoman R. B.: Washington D.C. AACC Press (1990)). Furthermore, special instruments are required for the assay due to the dry chemistry, and thus the Ektachem method lacks the versatility in simultaneous multiphasic assay of a large number of samples as in the multiphasic assay in the clinical laboratory test, as another disadvantage.

Another practical method for assaying bilirubin fractions was proposed by Akira Kosaka: Seibutsu Shiryo Bunseki (Biological Sample Analysis), 9 (3), 15–23 (1986); JP-A-62-105047) or by Umachi et al (Hisami Umachi: Rinsho Byori (Clinical Pathology), 37 (8), 905–910 (1989)).

According to the Kosaka et al method, bilirubin oxidase derived from *Myrothecium verrucaria* is made to act on a sample at pH 10.0 to eliminate the β and γ fractions by oxidation, and then only the δ fraction is subjected to diazo coloration by direct diazo reaction for assaying, or both α and δ fractions are subjected to diazo coloration by indirect diazo reaction (diazo reaction in the presence of a reaction accelerator such as alcohol, etc.) for assay and the assay result is subtracted from the assay result of total bilirubin concentration or the assay result of direct bilirubin concentration, whereby concentrations of the α fraction and the β+γ fraction as well as the δ fraction can be determined.

However, the Kosaka et al method suffers from such inconveniences that at the same time of eliminating the β and γ fractions by oxidation with the bilirubin oxidase derived from *Myrothecium verrucaria*, a portion of the α fraction is likewise eliminated by oxidation; a portion of the α fraction also undergoes diazo coloration during the direct diazo reaction; the degree of reaction differs between the direct reaction and the indirect reaction in the diazo coloration of the δ fraction, which result in very complicated errors in the assay results, showing a tendency of deviation of assayed δ fraction concentration from that of the HPLC method (Akira Kosaka: Seibutsu Shiryo Bunseki (Biological Sample Analysis), 9 (3), 15–23 (1986); John J. Lauff: Clin. Chem., 28 (4), 629–637 (1982); Lo H. D.: Clim., 29, 31–36 (1983)).

The Kosaka et al method is of multi-stage reaction process and basically manual assay is obligatory. Thus, the method is not applicable to an all-purpose, two-reagent automatic analyzer and lacks simplicity.

According to the Umachi et al method, on the other hand, bilirubin oxidase derived from *Trachyderma tsunodae* is made to act on a sample at pH 8.0 in the presence of salicylic acid to eliminate the α, β and γ fractions by oxidation and only the δ fraction is subjected to diazo coloration by diazo reaction for assay. Assay of the individual fractions can be carried as in the Kosaka et al method, that is, concentrations of the α fraction and the β+γ fraction as well as the δ fraction can be determined from the assay result of δ fraction concentration or by subtraction from the assay result of total bilirubin fraction concentration or assay result of direct bilirubin fraction concentration.

In the Umachi et al method, bilirubin oxidase derived from *Trachyderma tsunodae* eliminates about 40% of the δ fraction in the presence of salicylic acid by oxidation and the exact determination of δ fraction is impossible to conduct. Furthermore, the method is also of multi-stage reaction process and basically manual assay is obligatory. Thus, the method is not applicable to an all-purpose automatic analyzer and lacks simplicity.

In the assay of serum bilirubin, as described above, the conventional diazo method cannot exactly reflect the state of disease in case of larger proportion of the δ fraction, but only assay results of bilirubin fractions can sensitively respond to the state of disease. Only technical break through to the assay of bilirubin fractions is obviously a development of simple method for assaying the δ fraction. However, in the daily clinical laboratory test, no suitable reagents for assaying the δ fraction have been available yet for an all-purpose two-reagent automatic analyzer capable of conducting simultaneous multi-item assay of a large number of samples. Thus, development of reagents capable of assaying the δ fraction with a high reliability for assay in the automatic analyzer has been keenly desired.

SUMMARY OF THE INVENTION

An object of the present invention is to provide a method for assaying bilirubin fractions and an assay kit suitable for an all-purpose, two-reagent type automatic analyzer capable of conducting simultaneous multi-item assay of a large number of samples in good correlation to the assay results of the HPLC method regarded so far as the standard method.

As a result of extensive studies of reaction conditions for promoting oxidation reaction of the individual α, β and γ fractions of bilirubin by bilirubin oxidase, while suppressing the oxidation of the δ fraction with the help of the HPLC analysis, the present inventors found that the presence of at least one of a cationic surfactant and a nonionic surfactant can suppress the oxidation of the δ fraction and can promote the oxidation of the α, β and γ fractions.

Furthermore, the present inventor found that, different from the bilirubin oxidase derived from *Myrothecium Verrucaria* and the bilirubin oxidase derived from *Trachyderma tsunodae*, a bilirubin oxidase derived from the genus Pleurotus undergoes no considerable inhibition in the presence of at least one of a cationic surfactant and a nonionic surfactant.

As a result of further studies on the basis of combination of these findings, the present inventors established the present invention of substantially complete oxidation of the α, β and γ fractions, while substantially suppressing the oxidation of the δ fraction.

That is, the present invention provides a method for assaying bilirubin fractions, which comprises the steps of:
  making a bilirubin oxidase incapable of oxidizing a bilirubin δ fraction but capable of oxidizing a bilirubin non-δ fractions in the presence of at least one of a cationic surfactant and a nonionic surfactant to act as an oxidizing agent on a living body fluid sample; and
  assaying an amount of reacted bilirubin non-δ fractions or unreacted bilirubin δ fraction, thereby determining a concentration of bilirubin non-δ fractions or bilirubin δ fraction in the living body fluid sample.

Furthermore, the present invention provides a method for assaying a concentration of a bilirubin δ fraction in a living body fluid sample, which comprises the steps of:
  i) making a reagent capable of reacting with total bilirubin to act on a living body fluid sample, thereby determining a concentration of total bilirubin;
  ii) making a bilirubin oxidase incapable of oxidizing a bilirubin δ fraction but capable of oxidizing a bilirubin non-δ fractions in the presence of at least one of a cationic surfactant and a nonionic surfactant as an oxidizing agent to act on the living body fluid sample and assaying an amount of reacted bilirubin non-δ fractions, thereby determining a concentration of bilirubin non-δ fractions; and
  iii) subtracting the concentration of bilirubin non-δ fractions obtained in the step ii) from the concentration of total bilirubin obtained in the step i), thereby obtaining a concentration of bilirubin δ fraction.

Furthermore, the present invention provides an assay kit for determining a concentration of bilirubin non-δ fractions or bilirubin δ fraction in a living body fluid sample, which comprises:
  i) at least one of cationic surfactant and a nonionic surfactant; and
    a bilirubin oxidase incapable of oxidizing a bilirubin δ-fraction but capable of oxidizing bilirubin non-δ fractions in the presence of at least one of the surfactants.

Still furthermore, the present invention provides use of a bilirubin oxidase incapable of oxidizing a bilirubin δ fraction but capable of oxidizing bilirubin non-δ fractions in the presence of at least one of a cationic surfactant and a nonionic surfactant in determination of a concentration of bilirubin δ fraction or bilirubin non-δ fractions in a living body fluid sample.

DETAILED DESCRIPTION OF THE INVENTION

Figure 1:
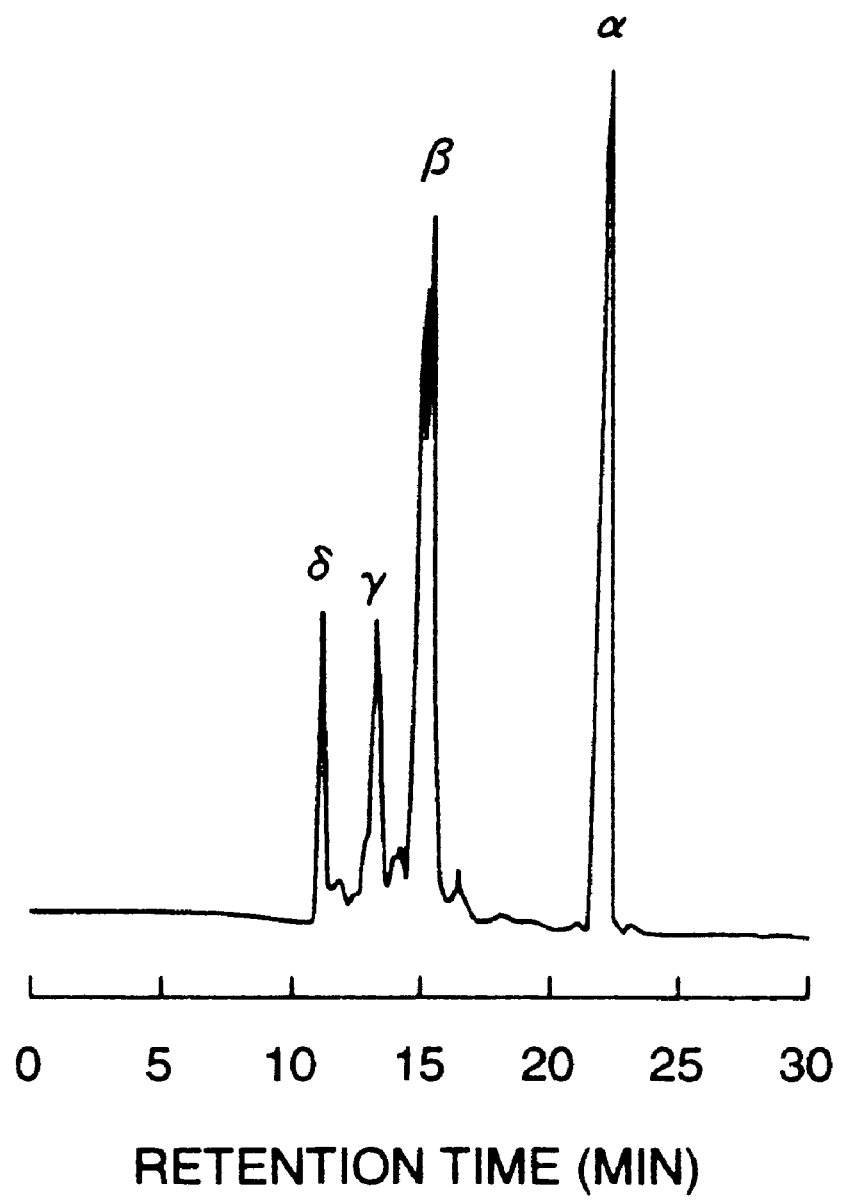
FIG. 1 shows a typical fractional pattern of a jaundice serum sample by bilirubin fractional analysis according to HPLC.

"Living body fluid sample" herein referred to means a sample available from a body fluid in the living body, including plasma, serum, urine, etc.

Cationic surfactants for use in the present invention preferably include quaternary ammonium salts represented by the following formulae (I), (II) and (III):

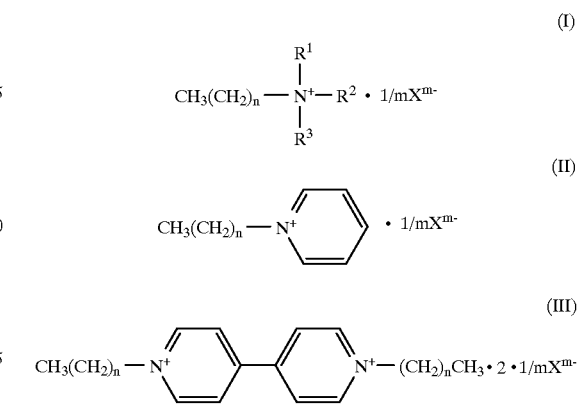

wherein $R^1$, $R^2$ and $R^3$ indepently represent an alkyl group having 1 to 10 carbon atoms, a cycloalkyl group having 5 to 10 carbon atoms, an aryl group having 6 to 10 carbon atoms or an aralkyl group having 7 to 10 carbon atoms; $X^{m-}$ represents an m-valent anion; and n represents an integer of 7 to 17.

In the foregoing formula (I), the alkyl group having 1 to 10 carbon atoms of $R^1$, $R^2$ and $R^3$ may be either straight or branched, and includes, for example, methyl, ethyl, n-propyl, isopropyl, n-butyl, isobutyl, sec-butyl, tert-butyl, pentyl, hexyl, octyl, etc.; the cycloalkyl group having 5 to 10 carbon atoms includes, for example, cyclopentyl, cyclohexyl, etc.; the aryl group having 6 to 10 carbon atoms includes, for example, phenyl, tolyl, xylyl, naphthyl, etc.; the aralkyl group includes, for example, benzyl, phenetyl, etc. $R^1$, $R^2$ and $R^3$ can be the same or different groups from one another.

In the foregoing formulae (I), (II) and (III), examples of $1/mX^{m-}$ include halide ions such as $F^-$, $Cl^-$, $Br^-$ and $I^-$; and $NO_3^-$, $1/2SO_4^{2-}$, $1/2SO_3^{2-}$, $CH_3SO_4^-$, p-toluene-sulfonate ion, etc. Groups represented by $CH_3(CH_2)_n-$ include, for example, decyl, dodecyl, tetradecyl, hexadecyl, octadecyl, etc.

Examples of quaternary ammonium salts represented by the foregoing formula (I) include alkyltrimethylammonium salts such as dodecyltrimethylammonium bromide, dodecyltrimethylammonium chloride, tetradecyltrimethylammonium bromide, tetradecyltrimethylammonium chloride, etc.; alkyltriethylammonium salts such as dodecyltriethylammonium chloride, tetradecyltriethylammonium chloride, etc.; alkyltripropylammonium salts such as dodecyltripropylammonium bromide, tetradecyltripropylammonium chloride, etc.; benzylammonium salts such as dodecyldimethylbenzylammonium chloride, tetradecyldimethylbenzylammonium chloride (Zephiramin) dodecyldiethylbenzylammonium chloride, tetradecyldiethylbenzylammonium chloride, etc.; and others.

Examples of quaternary ammonium salts represented by the foregoing formula (II) include alkylpyridinium salts such as decylpyridinium chloride, dodecylpyridinium chloride, tetradecylpyridinium chloride, cetylpyridinium bromide, etc.; and others.

Examples of quaternary ammonium salts represented by the foregoing formula (III) include alkylbipyridinium salts such as decylbipyridinium chloride, dodecylbipyridinium bromide, tetradecylbipyridinium bromide, etc.; and others.

Among the above-mentioned cationic surfactants, alkyltrimethylammonium salts are preferable, and alkyltrimethylammonium salts of $C_{12}$–$C_{16}$ are particularly preferable. The above-mentioned cationic surfactants can be used alone or in combination of two or more thereof.

Preferable nonionic surfactants for use in the present invention are those whose polyoxyethylene chain can serve as a hydrophilic domain. Such nonionic surfactants include, for example, polyoxyethylene (n-alkyl or iso-alkyl) ethers such as polyoxyethylene (iso-alkyl) ether (Adekatol SO-135, trademark of a product commercially available from Asahi Denka Kogyo K.K., Japan), polyoxyethylene (n-alkyl) ether (Emulgen 707, trademark of a product commercially available from Kao Corp., Japan), polyoxyethylenecetyl ether (Brij 58, trademark of a product commercially available from Aldrich Chemical Co., Inc., U.S.A.), etc.; polyoxyethylene (n-alkylphenyl or iso-alkylphenyl) ethers such as polyoxyethylene (n-nonylphenyl) ether (Adekatol NP-675, trademark of a product commercially available from Asahi Denka K.K., Japan), polyoxyethyleneisooctylphenyl ether (Triton X-100 and X-40S, trademarks of products commercially available from Rhom & Haas K.K., Japan), etc.; nonionic surfactants having a polyoxyethylene-polyoxypropylene block copolymer structure such as polyoxyethylene-polyoxypropylene condensate (Pullonic F68, trademark of a product commercially available from Asahi Denka K.K., Japan), polyoxypropylene-polyoxyethylene condensate of ethyldiamine (Tetronic 704, trademark of a product commercially available from Asahi Denka K.K., Japan), etc.; glycoside compounds such as octyl glucoside, octyl thioglucoside, octyl maltoside, etc.; and others.

Among others, polyoxyethylene (n-alkyl or iso-alkyl) ethers are preferable. The above-mentioned nonionic surfactants can be used alone or in combination of two or more thereof.

In the present invention, it is preferable to use the above-mentioned cationic surfactant alone or a combination of the cationic surfactant and the above-mentioned nonionic surfactant. Combination of both cationic and nonionic surfactants is particularly preferable, because of its synergistic effect as shown in Examples which follow.

Bilirubin oxidase for use in the present invention is a bilirubin oxidase substantially incapable of oxidizing a biliburin δ fraction but substantially completely capable of oxidizing biliburin non-δ fractions (α, β and γ fractions) in the presence of at least one of a cationic surfactant and a nonionic surfactant, and any biliburin oxidase can be used, so far as it has such properties as mentioned above.

Such a biliburin oxidase can be obtained, for example, from Bosidiomycetes capable of producing a biliburin oxidase having such properties as mentioned above. Preferable bilirubin oxidase can be derived from the genus Pleurotus such as *Pleurotus ostreatus* IFO 9669 strain; the genus Melanoleuca such as *Melanoleuca melaleuca* B-43 FERM BP-570 strain, etc.; or the genus Agaricus such as *Agaricus bisporus* IFO 30774 strain, etc. which all belong to Basidiomycetes. Bilirubin oxidase derived from the genus Pleurotus is particularly preferable.

The present invention is based on the finding that the above-mentioned bilirubin oxidase is made to act as an oxidizing agent on a living body fluid sample containing bilirubin in the presence of at least one of the above-mentioned cationic surfactant and nonionic surfactant, whereby the α, β and γ fractions can be substantially completely oxidized, while substantially suppressing oxidation of bilirubin δ fraction in the living body fluid sample. Thus, after the action of bilirubin oxidase on the living body fluid sample, the amount of reacted bilirubin non-δ fractions (α, β and γ fractions) or the amount of unreacted bilirubin δ fraction is measured, whereby the concentration of bilirubin non-δ fractions or bilirubin δ fraction in the living body fluid sample can be exactly determined.

When the concentration of at least one of the cationic surfactant and nonionic surfactant for use in the reaction of bilirubin oxidase with a living body fluid sample is too low, the satisfactory effect of suppression on the oxidation of bilirubin δ fraction and the satisfactory effect of promotion on the oxidation of bilirubin α, β and γ fractions cannot be obtained, whereas too high a concentration will intensify the inhibition of bilirubin oxidase activity to hinder the oxidation. Thus, the concentration range in the reaction solution is preferably 0.01 to 10%, more preferably 0.02 to 5%, particularly preferably 0.05 to 2%, wherein % is by weight on the basis of the reaction solution.

Bilirubin oxidase can be used preferably at a concentration of 0.1 to 10 KU/l, preferably 0.5 to 5 KU/l in the reaction solution.

The pH range of the reaction solution is not particularly limited during the reaction of bilirubin oxidase, so long as it can maintain the enzymatic activity, and is preferably 4.0 to 9.0, particularly 5.5 to 7.5.

Temperature for the reaction of bilirubin oxidase is usually 25° to 40° C. and the reaction time is usually 3 to 15 minutes.

In the present invention, ordinary reagents applicable to the assay of living body fluid components, such as buffer species, antiseptics, chelating agents, etc. can be used upon proper selection according to the known procedure.

After the action of bilirubin oxidase on a living body fluid sample, the amount of reacted bilirubin non-δ fractions or unreacted δ fraction can be determined preferably by measuring, for example, optical changes of living body fluid sample, because an automatic analyzer can be used for the measurement. Particularly, the amount can be determined by measuring changes in absorbancy in the wavelength range of 430 to 460 nm due to bilirubin, usually at 450 nm.

The present invention can be carried out, for example, in the following manner:

To determine the concentration of bilirubin non-δ fractions on the basis of optical changes of a living body fluid sample, a first reagent solution containing at least one of a cationic surfactant and a nonionic surfactant is mixed with a living body fluid sample containing bilirubin, such as plasma, serum, urine, etc., and then an absorbance in a wavelength range (430 to 460 nm) due to bilirubin in the solution is measured (Absorbance 1). Then, a second reagent solution containing a bilirubin oxidase is added to the solution to conduct oxidation of bilirubin at 25° to 40° C. for 3 to 15 minutes. Then, an absorbance in the wavelength range (430 to 460 nm) due to the bilirubin in the solution is measured again (Absorbance 2). After making a liquid volume correction, etc. on the measured Absorbances 1 and 2, a change in the absorbance before and after the oxidation is obtained. A concentration of bilirubin non-δ fractions in the living body fluid sample can be determined from the thus obtained change in the absorbance and a calibration curve prepared in advance in the same manner as above on the basis of changes in the absorbance in standard solution having known bilirubin concentrations. Such determination of concentration of bilirubin non-δ fraction can be carried out in an automatic analyzer.

Concentration of bilirubin δ fraction in a living body fluid sample can be obtained by determining a concentration of total bilirubin in the living body fluid sample in advance and then subtracting the concentration of bilirubin non-δ fractions as obtained above from the concentration of total bilirubin.

Concentration of total bilirubin can be determined according to the so far well known methods, for example, a method for measuring optical changes of a living body fluid sample (changes in the absorbance at 430 to 460 nm, usually at 450 nm) upon action of vanadic acid as an oxidizing agent (JP-A-5-18978), a method for measuring optical changes of a living body fluid sample (changes in the absorbance at 430 to 460 nm, usually at 450 nm) upon action of nitrous acid as an oxidizing agent (WO96/17251), a method for measuring an amount of azo coloring matters formed by reaction of a diazo reagent with a living body fluid sample in the presence of a reaction accelerator (Clin. Chem., 19, 984–993 (1973)), etc., or furthermore by a method for measuring optical changes of a living body fluid sample (changes in the absorbance at 430 to 460 nm, usually at 450 nm) upon action of a bilirubin oxidase as an oxidizing agent (Billy Perry, Basil T. Doumag et al.: Clin. Chem., 32 (2), 329–332 (1986); Shogo Otsuji et al.: Clin. Biochem., 21, 33–38 (1988)).

Alternatively bilirubin δ fraction in a living body fluid sample can be assayed by direct measurement without determining the concentration of total bilirubin, i.e., by determining an amount of unreacted δ bilirubin fraction remaining from the action of bilirubin oxidase on the living body fluid sample in the presence of at least one of a cationic surfactant and a nonionic surfactant according to the above-mentioned known methods, for example, the method for measuring optical changes (changes in the absorbance at 430 to 460 nm, usually at 450 nm) of a sample, using vanadic acid or nitrous acid or the method using a diazo reagent. In that case, it is important to select an oxidizing agent capable of oxidizing δ bilirubin fraction even in the presence of the surfactant.

Alternatively, concentrations of bilirubin non-δ fractions and bilirubin δ fraction can be also determined by subjecting a living body fluid sample to HPLC analysis according to the known HPLC method (John J. Lauff: J. Chromatogr., 226, 391–402 (1981); Nakamura H.; Bunsekikagaku, 86, 352–355 (1987); Yukihiko Adachi: Gastroeuterologia Japonica, 23 (2), 268–272 (1988); Yuko Kato; Medical Journal of Kinki University, 14 (1), 97–112 (1989)) before and after action of bilirubin oxidase on the living body fluid sample in the presence of at least one of a cationic surfactant and a nonionic surfactant, respectively, and making corresponding comparison of the analytical measurements obtained before and after the action of bilirubin oxidase.

As is obvious from the foregoing, the present invention provides an assay kit for determining a concentration of bilirubin non-δ fraction or bilirubin δ fraction in a living body fluid sample, which comprises:

i) at least one of the above-mentioned cationic surfactant and nonionic surfactant; and ii) the above-mentioned bilirubin oxidase incapable of oxidizing the bilirubin δ fraction but capable of oxidizing the bilirubin non-δ fractions in the presence of the surfactant. Besides these essential components, the assay kit may further contain ordinary reagents for use in assaying the ordinary living body fluid components, for example, a buffer solution, an antiseptic, a chelating agent, a diluent, etc. Preferably, the assay kit may be adjusted to application to an automatic analyzer.

As described above, concentration of bilirubin non-δ fractions or furthermore bilirubin δ fraction in a living body fluid sample can be directly determined according to the present invention. The determination can be made without addition of any assaying reagent to the living body fluid sample and any special physical separation means. Furthermore, the determination can be made by measuring optical changes of a living body fluid sample and thus can be made by an automatic analyzer. When assaying of bilirubin non-δ fractions or bilirubin δ fraction of a living body fluid sample is carried out with reagents for determining the bilirubin non-δ fractions or bilirubin δ fraction according to the present invention in an automatic analyzer together with the conventional assaying of total bilirubin or direct bilirubin, useful information on $\delta/(\beta+\gamma+\delta)$, $(\beta+\gamma)/\delta$, etc. can be simply obtained by the intercomputable function of the automatic analyzer on the basis of the concentrations of α fraction, $(\beta+\gamma)$ fraction and $(\beta+\gamma+\delta)$ fraction obtained from combinations of assay values of the bilirubin non-δ fractions or bilirubin δ fraction with the assay values of total or direct bilirubin.

PREFERRED EMBODIMENTS OF THE INVENTION

The present invention will be described in detail below, referring to Reference Example, Examples and Drawings, but the present invention is not limited thereto.

Reference Example
Bilirubin Fractional Analysis by HPLC

Bilirubin fractional analysis by HPLC was carried out according to Lauff et al method (John J. Lauff: Clin. Chem., 28 (4) 629–697 (1982)), wherein untreated serum samples were analyzed without salting-out by sodium sulfate, because the individual bilirubin fractions were to be prevented from denaturing, though globulins were adsorbed on the column from the samples to promote column deterioration.

For HPLC, a Hitachi HPLC system (Column Oven L-7300, UV Detector L-7400, Pump L-7100 and Integrator D-7500) was used in connection to a reversed phase chromatography-based column (Lichrospher 100 RP-18 (10 $\mu$m), commercially available from Kanto Kagaku Co., Ltd., Japan).

Bilirubin fractions were eluted by linear gradient elution by isopropanol between two solutions, i.e. Solution A (purified water/2-methoxyethanol, of 950/50 by volume, adjusted to pH 2.1 by phosphoric acid) and Solution B (isopropanol/2-methoxyethanol/phosphoric acid of 950/50/2.5 by volume) and detected at a wave-length of 450 nm.

Typical fractional pattern of a jaundice serum sample by bilirubin fractional analysis by HPLC is shown in FIG. 1, wherein $\delta$ fractions of $\alpha$ to $\delta$ can be shown, as already reported.

According to the present invention, 480 $\mu$l of a buffer solution (R-1) containing at least one of a cationic surfactant and a nonionic surfactant is added to 16 $\mu$l of a serum sample, followed by heating at 37° C. for 5 minutes. Then, 120 $\mu$l of an isotonic sodium chloride solution was further added thereto, followed by heating at 37° C. for 5 minutes. Then, 100 $\mu$l of a filtrate through a 0.45 $\mu$m pore size membrane filter from the resulting mixture is introduced into the column. In case of assaying the individual fractions by oxidation with a bilirubin oxidase, assaying is carried out in the same manner as above, except that 120 $\mu$l of a buffer solution (R-2) containing bilirubin oxidase was used in place of the isotonic sodium chloride solution, as shown in the following Examples.

EXAMPLE 1
Promotion of Oxidation of $\alpha$, $\beta$ and $\gamma$ Fractions and Suppression of Oxidation of $\delta$ Fraction by Additives Additives having an influence on promotion of oxidation of $\alpha$, $\beta$ and $\gamma$ fractions and suppression of oxidation of $\delta$ fraction on the basis of bilirubin oxidase (commercially available from K.K. Seishin, Japan) derived from *Pleurotus ostreatus* IFD 9669 strain were screened under the following reagent conditions:

| First reagent: | Potassium hydrogen phtalate: 50 mM + various additives pH: 5.5 |
|---|---|
| Second reagent: | Isotonic sodium chloride solution containing 6 KU/l of bilirubin oxidase |

Bilirubin-high content pool serum was subjected to reaction according to the same method as in Reference Example, using the first reagent as R-1 and the second reagent as R-2, and then subjected to bilirubin fractional analysis by HPLC. Peak areas of $\alpha$ and $\delta$ fractions were obtained from the resulting fractional pattern and compared with the peak areas of the corresponding fractions before the reaction (case of using the single isotonic sodium chloride solution as R-2) to study influences of additives on the oxidation of $\alpha$ and $\delta$ fractions. It was found that peaks of $\beta$ and $\gamma$ fractions all disappeared after the reaction. Peak areas of fractions after the reaction were calculated as residual rates (%) on the basis of the peak areas of the corresponding fractions before the reaction as 100. The results are shown in Table 1.

TABLE 1

Promotion of oxidation of $\alpha$ fraction and suppression of oxidation of $\delta$ fraction by additives

| | | | Residual rate (%) | | | |
|---|---|---|---|---|---|---|
| No. | Additive | Concentration | $\alpha$ fraction | $\beta$ fraction | $\gamma$ fraction | $\delta$ fraction |
| No surfactant added | | | | | | |
| 1. | None | | 27 | 0 | 0 | 44 |
| 2. | Thiourea | 20 mM | 37 | 0 | 0 | 42 |
| 3. | Hydrazine | 20 mM | 13 | 0 | 0 | 29 |
| 4. | BSA | 0.5% | 24 | 0 | 0 | 60 |
| 5. | PVP | 1.0% | 35 | 0 | 0 | 49 |
| 6. | Lithium chloride | 250 mM | 42 | 0 | 0 | 39 |
| Cationic surfactant added | | | | | | |
| 7. | Dodecyltrimethyl-ammonium bromide | 1.0% | 0 | 0 | 0 | 55 |
| 8. | Tetradecyltrimethyl-ammonium bromide | 1.0% | 0 | 0 | 0 | 63 |
| Nonionic surfactant added | | | | | | |
| 9. | Brij-58 | 1.0% | 0 | 0 | 0 | 46 |
| 10. | Tetronic 704 (Asahi Denka) | 1.0% | 5 | 0 | 0 | 43 |
| 11. | Octyl glucoside | 1.0% | 21 | 0 | 0 | 41 |
| 12. | Adekatol SO-135 (Asahi Denka) Emulgen 707 (Kao) | 0.2% 0.2% | 0 | 0 | 0 | 65 |
| 13. | Adekatol SO-135 (Asahi Denka) Emulgen 707 (Kao) | 0.5% 0.5% | 0 | 0 | 0 | 64 |
| Both cationic and nonionic surfactants added | | | | | | |
| 14. | Cetylpyridinium bromide Brij-58 | 1.0% 1.0% | 0 | 0 | 0 | 71 |
| 15. | Zephilamin Brij-58 | 1.0% 1.0% | 0 | 0 | 0 | 76 |
| 16. | Tetradecyltrimethyl-ammonium bromide Brij-58 | 1.0% 1.0% | 0 | 0 | 0 | 93 |
| 17. | Tetradecyltrimethyl-ammonium bromide Brij-58 Adekatol SO-135 (Asahi Denka) Emulgen 707 (Kao) | 1.0% 1.0% 0.2% 0.2% | 0 | 0 | 0 | 97 |

As is apparent from Table 1, addition of at least one of the cationic surfactant and the nonionic surfactant can suppress oxidation of $\delta$ fraction and promote oxidation of $\alpha$, $\beta$ and $\gamma$ fractions.

EXAMPLE 2
Difference in Reactivity by Origins of Bilirubin Oxidase

Oxidation states of the individual bilirubin fractions by bilirubin oxidase derived from *Myrothecium verrucaria* (commercially available from Amano Seiyaku K.K., Japan), bilirubin oxidase derived from *Trachyderma tsunodae*

(commercially available from Takara Shuzo Co., Ltd., Japan), and bilirubin oxidase derived from *Pleurotus ostereatus* (commercially available from K.K. Seishin, Japan) in the presence of at least one of cationic surfactants and nonionic surfactants under the following reagent conditions were analyzed by HPLC fractional analysis.

| First reagent (R-1): | Potassium hydrogen phthalate | 50 mM |
|---|---|---|
| | Tetradecyltrimethylammonium bromide | 1% |
| | Brij-58 | 1% |
| | Adekatol SO-135 (Asahi Denka) | 0.2% |
| | Emulgen 707 (Kao) | 0.2% |
| | BSA | 0.5% |
| | PH: 5.5 | |
| Second reagent (R-2): | Isotonic sodium chloride solution containing 6 KU/l of bilirubin oxidase of one of the origins | |

Figure 2:
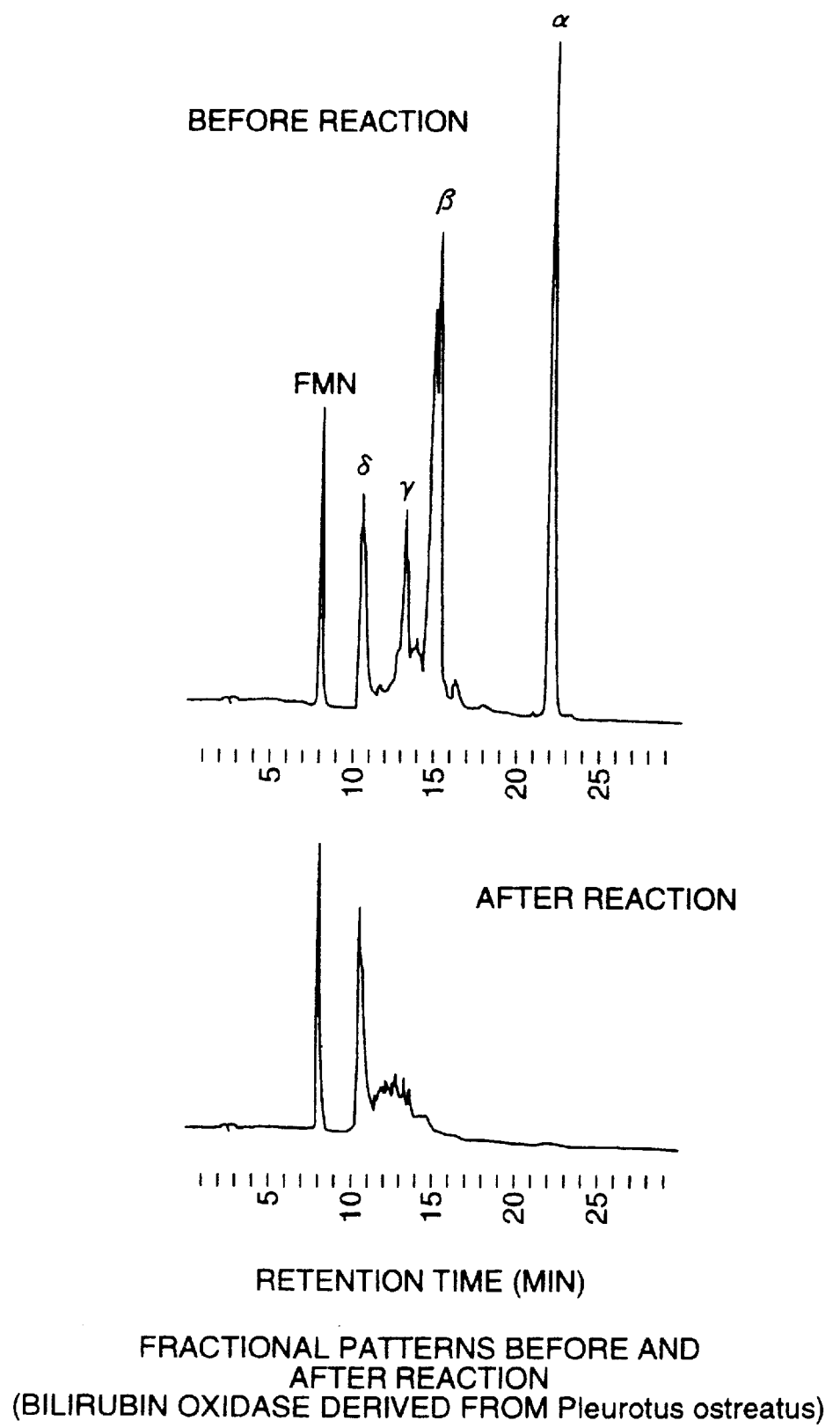
FIG. 2 shows fractional patterns before and after reaction of a jaundice serum sample according to the present invention, respectively.

Bilirubin-high content pool serum was subjected to reaction according to the same method as in Reference Example and then subjected to bilirubin fractional analysis by HPLC. Peak areas of individual fractions were obtained from the resulting fractional pattern and compared with the peak areas of the corresponding fractions before the reaction (case of using single isotonic sodium chloride solution as R-2) to study the oxidation states of the individual fractions. Peak areas of fractions after the reaction were calculated as residual rate (%) on the basis of the peak areas of the corresponding fractions before the reaction as 100. The results are shown in Table 2. In FIG. 2 are shown fractional patterns before the reaction and after the reaction with bilirubin oxidase derived from *Pleurotus ostreatus* (commercially available from K.K. Seishin, Japan), respectively.

TABLE 2

Difference in reactivity by origins of bilirubin oxidase

| | Residual rate (%) | | | |
|---|---|---|---|---|
| Origin of bilirubin oxidase | α fraction | β fraction | γ fraction | δ fraction |
| Before reaction | 100 | 100 | 100 | 100 |
| *Myrothecium verrucaria* | 77 | 58 | 73 | 87 |
| *Trachyderma tsunodae* | 94 | 77 | 90 | 100 |
| *Pleurotus ostreatus* | 0 | 0 | 0 | 97 |

As is evident from Table 2 and FIG. 2, reaction by bilirubin oxidase derived from *Myrothecium verrucaria* (commercially available from Amano Seiyaku K.K., Japan) and bilirubin oxidase derived from *Trachyderma tsunodae* (commercially available from Takara Shuzo Co., Ltd., Japan) was considerably hindered in the presence of at least one of cationic surfactants and nonionic surfactants, and the individual bilirubin fractions could not be oxidized, whereas bilirubin oxidase derived from *Pleurotus osteatus* (commercially available from K.K. Seishin, Japan) could substantially completely oxidize the α, β and γ fractions without any hinderance to the reaction, and substantially 100% of the δ fraction remained.

EXAMPLE 3

Correlation Between the Present Invention and the Conventional HPLC Method

Twenty five serum samples were subjected to bilirubin fractional analysis by HPLC according to the same method as in Reference Example 1. Ratios of peak area ($\alpha+\beta+\gamma$) corresponding to the bilirubin non-δ fractions to total peak area were obtained from the respective fractional patterns, and multiplied by assay values of total bilirubin concentration to obtain concentrations of bilirubin non-δ fractions by HPLC. Correlation of concentrations of bilirubin non-δ fractions determined by the present method to the concentrations of non-δ fractions by HPLC is shown in FIG. 3.

Furthermore, ratios of peak area (δ) corresponding to the bilirubin δ fraction to total peak area were obtained from the respective fractional patterns, and multiplied by assay values of total bilirubin concentration to obtain concentrations of bilirubin δ fraction by HPLC. Correlation between the concentrations of bilirubin δ fraction obtained by subtracting the concentrations of bilirubin non-δ fractions determined by the present method from the concentrations of total bilirubin, respectively, and the concentrations of bilirubin δ fraction by HPLC is shown in FIG. 4.

Figure 3:
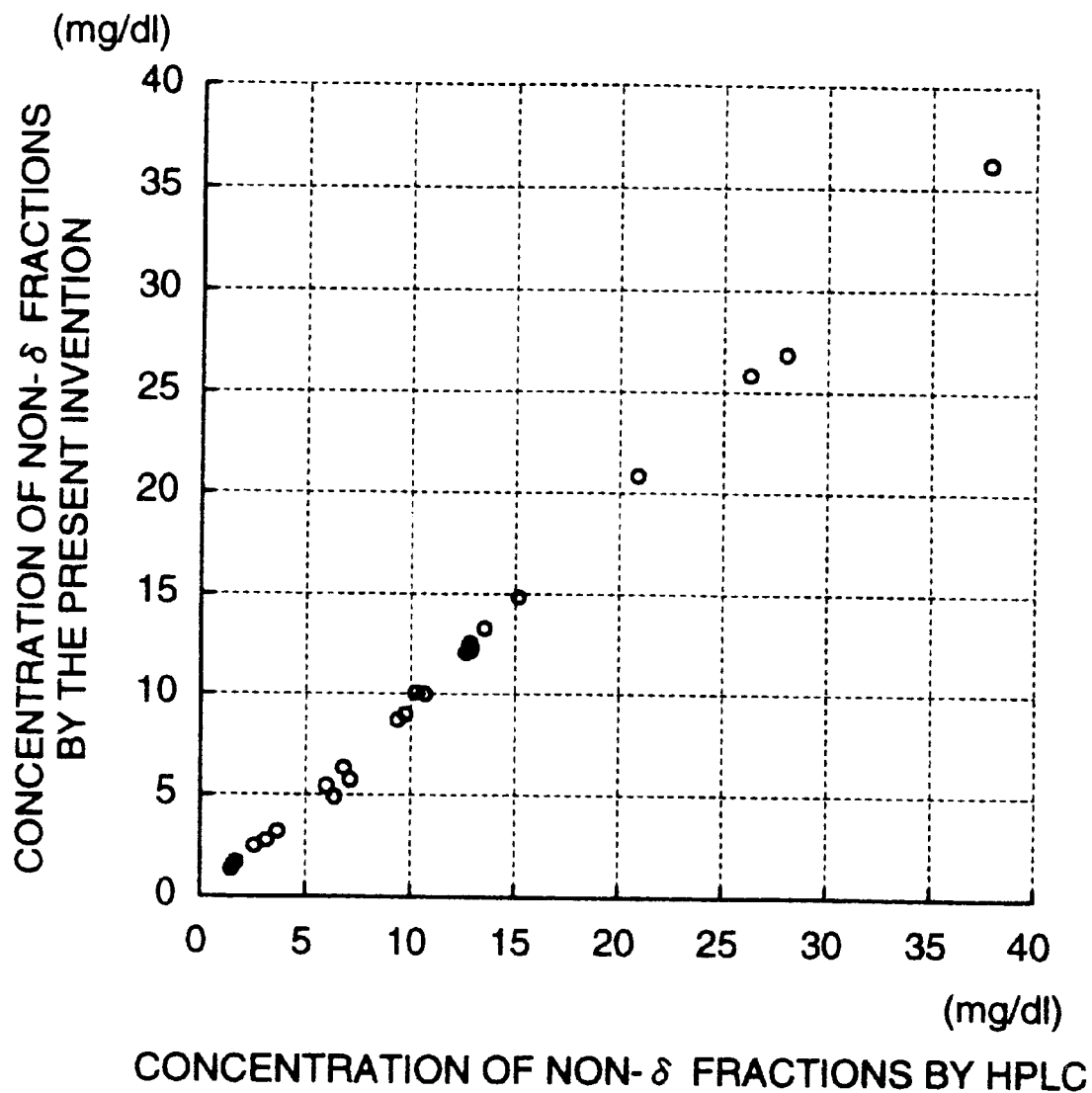
FIG. 3 shows a correlation between concentrations of bilirubin non-δ fractions according to HPLC (conventional method) and those according to the present invention.

As is evident from FIG. 3, the concentrations of bilirubin non-δ fractions by HPLC and those by the present invention have a very good correlation as given by a regression equation $Y=0.98X-0.29$ and by a correlation coefficient $r=0.999$, showing the exactness of assay results of the present method.

Figure 4:
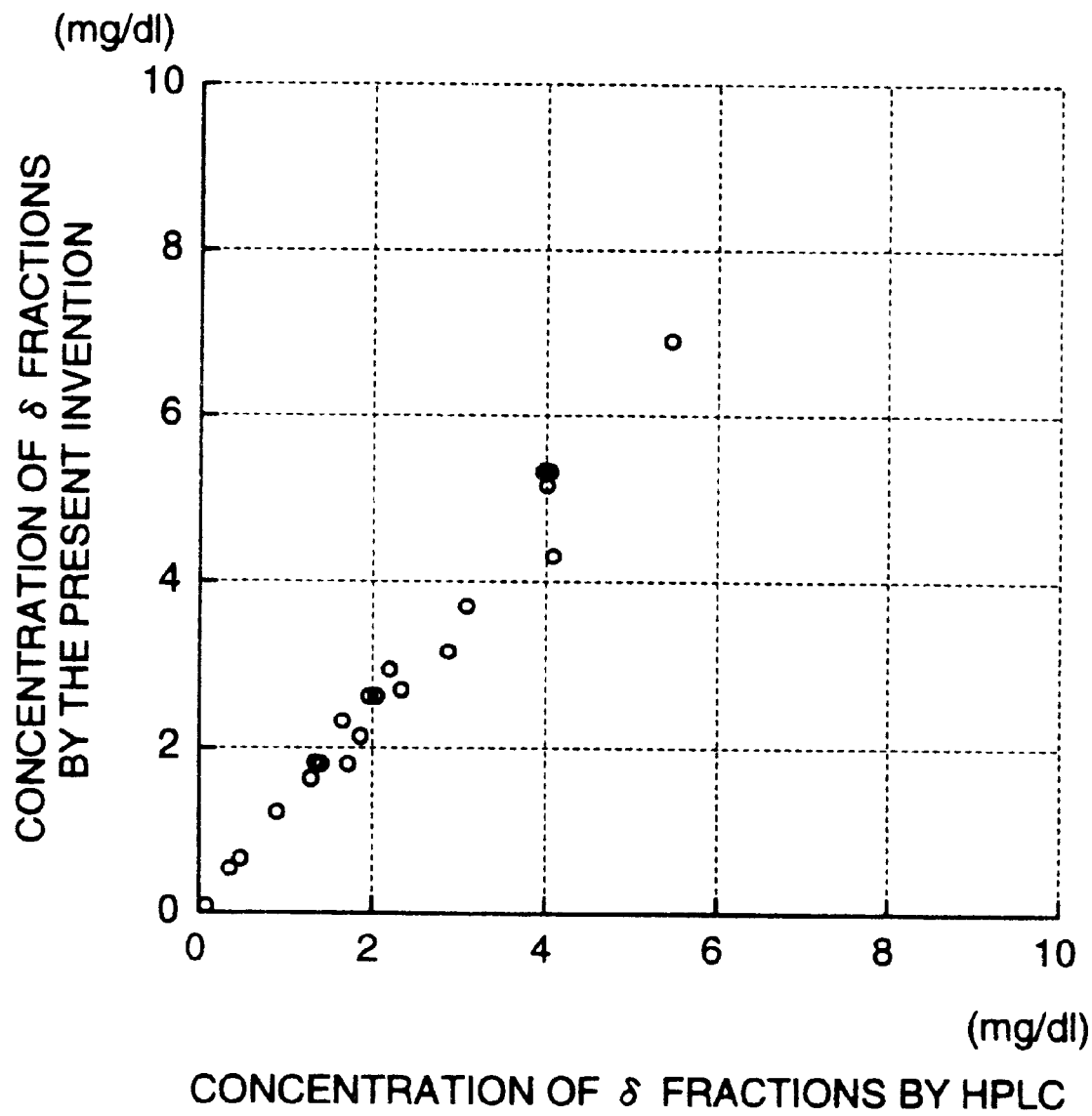
FIG. 4 shows a correlation between concentrations of bilirubin δ fraction according to HPLC (conventional method) and those according to the present invention.

As is evident also from FIG. 4, the concentrations of bilirubin δ fraction by HPLC and those by the present method have a very good correlation as given by a regression equation $Y=1.23X-0.04$ and by a correlation coefficient $r=0.990$, further showing the exactness of assay results of the present method.

Difference in inclination by 23% seems due to a particularly large fluctuation in the molar extinction coefficient in the hydrophilic fractions because of the presence of the individual fractions in the organic solvent having a concentration gradient under the HPLC eluting conditions.

Method for determining a concentration of total bilirubin and the present method for determining a concentration of bilirubin non-δ fractions as used above will be described below:

(1) Method for determining a concentration of total bilirubin:

Method for determining concentrations of total bilirubin and direct bilirubin on the basis of the nitrous acid oxidation method, which can obtain assay results equivalent to those by the diazo method and has overcome various problems of the diazo method, was disclosed by the present inventors (WO96/17251). Concentration of total bilirubin was determined by the nitrous acid oxidation method using the following reagents under the following assay conditions:

Assay reagent: N-assay L T-Bil Nittobo (commercially available from Nitto Boseki Co., Ltd., Japan)

First reagent (R-1): 100 mM citric acid buffer solution (pH 3.70)

Second reagent (R-2): 5 mM sodium nitrite solution

Assay Conditions

In an automatic analyzer (Hitachi Model 7150, commercially available from Hitachi Ltd., Japan), changes in the absorbance at main wavelength of 450 nm and subwavelength of 546 nm were measured by a 2-point and method for 8 μl of R-1, and concentrations of total bilirubin in samples were determined from a calibration curve based on changes in the absorbance of bilirubin in the standard solution.

That is, to determine a concentration of total bilirubin, the first reagent (R-1) of the commercially available assay reagent and a serum sample were mixed together in the automatic analyzer, followed by incubation at 37° C. for 5 minutes, and then the absorbance due to the bilirubin in the solution was measured at main wavelength of 450 nm and subwavelength of 546 nm (Absorbance 1). Then, the second reagent containing the nitrite of the commercially available assay reagent was added to the solution, followed by oxidation of bilirubin at 37° C. for 5 minutes, and then absorbance due to the bilirubin in the solution was again measured (Absorbance 2). The assay values of Absorbances 1 and 2 were subjected to liquid volume correction, etc. and then a change in the absorbance before and after the oxidation was determined. Concentration of total bilirubin in the sample was determined from the thus determined change in the absorbance and a calibration curve prepared in advance on the basis of changes in the absorbance obtained in the same manner as above, using the standard solution having a known bilirubin concentration.

(2) Method for determining a concentration of bilirubin non-δ fractions:

Concentration of bilirubin non-δ fractions in serum samples was determined under the following reagent conditions:

| First reagent (R-1): | Potassium hydrogen phthalate | 50 mM |
| | Tetradecyltrimethylammonium bromide | 1% |
| | Brij-58 | 1% |
| | Adekatol SO-135 (Asahi Denka) | 0.2% |
| | Emulgen 707 (Kao) | 0.2% |
| | BSA | 0.2% |
| | pH 5.5 | |
| Second reagent (R-2): | Isotonic sodium chloride solution containing 6 KU/l of bilirubin oxidase (derived from *Pleurotus ostreatus*) | |

Assay Conditions

Determination was made under the same assay conditions as in (1) method for determining a concentration of total bilirubin except that the above-mentioned first and second reagents were used as the assay reagent.

What is claimed is:

1. A method for assaying a bilirubin δ fraction or bilirubin non-δ fractions in a living body fluid sample, which comprises the steps of:

reacting as an oxidizing agent a bilirubin oxidase, which is derived from the genus Pleurotus, Melanoleuca or Agaricus and which is incapable of oxidizing a bilirubin δ fraction but capable of oxidizing bilirubin non-δ fractions in the presence of at least one of a cationic surfactant and a nonionic surfactant selected from the group consisting of a polyoxyethylene (n-alkyl) ether, a polyoxyethylene (iso-alkyl) ether, a polyoxyethylene (n-alkylphenyl) ether and a polyoxyethylene (iso-alkylphenyl) ether, with the living body fluid sample in the presence of at least one of said cationic surfactant and nonionic surfactant, wherein said at least one catonic surfactant or nonionic surfactant is at a concentration effective to suppress the bilirubin δ oxidation; and determining an amount of the thus oxidized bilirubin non-δ fractions or unoxidized bilirubin δ fraction, thereby obtaining a concentration of the bilirubin non-δ fractions or a concentration of the bilirubin δ fraction in the living body fluid sample.

2. A method according to claim 1, wherein the cationic surfactant is alkyltrimethylammonium salt.

3. A method according to claim 1, wherein the nonionic surfactant is a nonionic surfactant whose polyoxyethylene chain serves as a hydrophilic domain.

4. A method according to claim 1, wherein the concentrations of reacted bilirubin non-δ fractions are determined by measuring optical changes of the living body fluid sample, or the concentration of unreacted δ bilirubin fraction is determined by measuring optical changes of the living body fluid sample.

5. A method for determining a concentration of a bilirubin δ fraction in a living body fluid sample, which comprises the steps of:

i) reacting a reagent capable of reacting with total bilirubin in the living body fluid sample, thereby determining a concentration of total bilirubin in the living body fluid sample;

ii) determining a concentration of bilirubin non-δ fractions in the living body fluid sample according to any one of the methods of claims 1 and 2 to 4; and iii) subtracting the concentration of bilirubin non-δ fractions determined in the step ii) from the concentration of total bilirubin determined in the step i), thereby obtaining a concentration of the bilirubin δ fraction in the living body fluid sample.

* * * * *

UNITED STATES PATENT AND TRADEMARK OFFICE
CERTIFICATE OF CORRECTION

PATENT NO. : 5,945,298
DATED : August 31, 1999
INVENTOR(S) : KOJIMA, et. al.

It is certified that error appears in the above-identified patent and that said Letters Patent is hereby corrected as shown below:

Title page, item [*] Notice: delete, This patent is subject to a terminal disclaimer.

Signed and Sealed this

Twelfth Day of September, 2000

Attest:

Q. TODD DICKINSON

Attesting Officer

Director of Patents and Trademarks